United States Patent [19]
Lopez, Jr. et al.

[11] Patent Number: 6,074,634
[45] Date of Patent: Jun. 13, 2000

[54] FEEDING ATTRACTANT AND STIMULANT FOR ADULT CONTROL OF NOCTUID AND/OR OTHER LEPIDOPTERAN SPECIES

[75] Inventors: Juan D. Lopez, Jr.; Ted N. Shaver; Kenneth R. Beerwinkle; Peter D. Lingren, all of College Station, Tex.

[73] Assignee: The United States of America as represented by the Secretary of Agriculture, Washington, D.C.

[21] Appl. No.: 09/166,655

[22] Filed: Oct. 5, 1998

Related U.S. Application Data

[60] Provisional application No. 60/061,005, Oct. 6, 1997.

[51] Int. Cl.$^7$ .......................... A01N 25/00; A01N 27/00; A01N 31/00; A01N 33/24; A01N 35/00; A01N 37/00; A01N 43/00

[52] U.S. Cl. .......................... 424/84; 424/405; 514/159; 514/160; 514/161; 514/162; 514/163; 514/164; 514/456; 514/461; 514/529; 514/530; 514/532; 514/543; 514/544; 514/546; 514/640; 514/681; 514/682; 514/690; 514/693; 514/699; 514/701; 514/703; 514/717; 514/720; 514/724; 514/729; 514/730; 514/731; 514/733; 514/739; 514/762; 514/763; 514/766; 514/964; 514/965

[58] Field of Search ..................... 424/84, 405; 514/449, 514/512, 529, 532, 549, 645, 679, 690, 699, 701, 703, 724, 728, 733, 739, 762, 763, 764, 766, 769, 770, 772, 772.2, 772.3, 772.4, 772.7, 777, 778, 781, 949, 975, 456, 461, 546, 640, 681, 682, 693, 717, 729, 730, 731, 159–164, 530, 543, 544, 964, 965; 43/107

[56] References Cited

U.S. PATENT DOCUMENTS

| | | | |
|---|---|---|---|
| 4,961,929 | 10/1990 | Gurvich et al. | 424/196.1 |
| 5,174,998 | 12/1992 | Ijitsu et al. | 424/410 |
| 5,665,344 | 9/1997 | Pair et al. | 424/84 |

FOREIGN PATENT DOCUMENTS

| | | |
|---|---|---|
| 9703561 | 2/1997 | WIPO . |

OTHER PUBLICATIONS

Wood, Floral Lures May Doom Earworm, Agricultural Research (Washington), vol. 39, No. 6, pp. 18–20, Jun. 1991.

Kint et al., Chemical Composition of *Guara suffulta* and *Gaura longiflora* Flower Volatiles, vol. 5, No. 2, pp. 201–203, Apr. 1993.

Ogata et al., Attractant for Bluegrass Webworm, JP408245310A, APS,GPI, JPO (Japanese Patent Abstracts), Abstract, Sep. 1996.

Teranishi et al., Chemical composition of Gaura drummondii flower volatiles (J. Essent. Oil Res., vol. 3, No. 4, pp. 287–288 (1991)), STN/CAS,CAPLUS, Abstract, 1992.

Chemical Abstracts vol. 127:217825, 1997.
Chemical Abstracts vol. 118:251437x, 1993.
Chemical Abstracts vol. 124:223639, 1996.
Chemical Abstracts vol. 124:3062, 1995.
Chemical Abstracts vol. 126:196434, 1997.
Chemical Abstracts vol. 102:57846j, 1985.
Chemical Abstracts vol. 101:85703h, 1984.
Chemical Abstracts vol. 95:75489m, 1981.

*Primary Examiner*—John Pak
*Assistant Examiner*—Frank Choi
*Attorney, Agent, or Firm*—M. Howard Silverstein; Randall E. Deck; John D. Fado

[57] ABSTRACT

The present invention provides an composition for attracting noctuid and/or other lepidopteran species. Liquid and solid formulations are provided, along with methods for their use, for controlling or eliminating noctuid and/or other lepidopteran species, and/or protecting plants susceptible to noctuid and/or other lepidopteran species damage.

17 Claims, 6 Drawing Sheets

Fig. 5 Moths Captured per Trap per Night, Melonworm

Fig. 6

FEEDING ATTRACTANT AND STIMULANT FOR ADULT CONTROL OF NOCTUID AND/OR OTHER LEPIDOPTERAN SPECIES

CROSS REFERENCE TO RELATED APPLICATIONS

This application hereby claims the benefit of U.S. provisional patent application Ser. No. 60/061,005, filed Oct. 6, 1997, the contents of which are incorporated by reference herein.

BACKGROUND OF THE INVENTION

1. Field of the Invention

This invention relates to a novel composition and its use as an attractant for both male and female noctuids and other lepidopteran pests.

2. Description of the Prior Art

Pesticide control of the Helicoverpa/Heliothis species such as the corn earworm (Helicoverpa zea [Boddie]) and the tobacco budworm (Heliothis virescens [F.]), as well as other lepidopteran pest species, is conventionally directed at the larvae which feed primarily on the fruiting parts of their host plants. Thus, conventional control practices have usually involved high volume broadcast applications of insecticides on a field by field basis. This trend has resulted in major concerns for environmental contamination and food safety among consumers.

Alternative control strategies involving the use of attract and kill technologies or attracticides, i.e., feeds/baits which are attractive and optionally toxic to the target insect species, for the highly mobile adults have advantages over conventional practices for managing Helicoverpa/Heliothis species. Joyce [pp. 173–188, In: Reed (Ed.) ICRISAT, Proceedings Nov. 15–20, 1981, Pantacheru, India (1982)] estimated that adults were 10 to 100 times more susceptible to insecticides than were larvae, and that adults were much less likely to develop resistance to insecticides. Adult females require a carbohydrate food source, usually obtained from plant nectars, to carry out normal reproductive functions. In addition, early post-emergence feeding on plant exudates and nectars is a high-priority activity for both male and female moths $\leq 1$ d of age [Lingren et al., pp. 73–77, In: Motes (Ed.), Proceedings 6th Annual Horticulture Industry Show, Tulsa, Okla., Oklahoma State University, Stillwater, 1987; Environ. Entomol., 17:254–258, 1988; and Beerwinkle et al., Environ. Entomol., 22:554–558, 1993]. Therefore, the availability of effective attracticides at emergence sites may have good potential for killing adults in their source zones before they can disperse and reproduce in new habitats. The successful development of attracticides and incorporation of this technology into adult management strategies will permit the reduction of corn earworm pest problems over large areas, while substantially reducing the total use of synthetic pesticides and exposure of human foods to pesticide contamination. The development of effective attractants/attracticides will also be useful in monitoring populations of noctuid and/or other lepidopteran pests.

Various natural and synthetic attractants have been used with some success in attracticide formulations to control and manage other insect pest species. Natural hydrolysates from hydrolyzed proteins of yeasts and corn or soybean bran have been used as attractants in toxic lures for various species of fruit flies (Diptera:Tephritidae) (Steiner, J. Econ. Entomol., 84:1672–1676, 1952; and Ayers, Proceedings Fla. State Hortic. Soc., 70:67–69, 1957). Progress of research to develop synthetic attractants that mimic the efficacy of protein hydrolysates for attracting various species of fruit flies has apparently been slow, but Wakahayashi & Cunningham (J. Econ. Entomol., 84:1672–1676, 1991) described a four-component synthetic bait that attracted both sexes of melon flies (Dacus cucurbitae Coquillett). Prokopy et al. (Environ. Entomol., 22:453–458, 1993) recently reported that excrement from various species of birds fed high-protein diets was more attractive to the Mediterranean fruit flies (Ceratitis capitata [Wiedemann]) than hydrolysates, and they predicted that chemically characterizing the bird excrements could lead to development of improved synthetic attractants for fruit fly pests.

Coppedge et al. (Environ. Entomol., 6:66–68, 1977; J. Econ. Entomol., 71:483–486, 1978) reported the successful development of an attracticide-based screwworm adult suppression system (SWASS). The SWASS units were composed of a volatile chemical formulation (Swormlure-2) which mimicked the attractiveness of decomposing liver, a food source that stimulated feeding, and an insecticide. The SWASS system was used to suppress the native populations of screwworm, (Cochliomyia hominivorax [Coquerel]) adults in areas where sterile males were later released to eradicate the populations.

Considerable research has been conducted to develop attracticide technology for various species of corn rootworms (Metcalf et al., J. Econ. Entomol., 80:870–875, 1987; Metcalf & Lampman, J. Econ. Entomol., 82:123–129,1989; Lance & Sutter, J. Econ. Entomol., 83:1085–1090, 1990; J. Econ. Entomol., 84:1861–1868, 1991; Hesler & Sutter, Environ. Entomol., 22:743–750, 1993; and Tallamy & Halaweish, Environ. Entomol., 22:925–932, 1993). Dry granular food baits containing insecticides and natural cucurbitacin feeding stimulants derived from plants of the family Cucurbitaceae have demonstrated effectiveness for controlling several species of corn rootworms. Apparently, cucurbitacins are powerful feeding stimulants for several species of rootworms, but cucurbitacins are not volatile; thus, they are not effective as long-range attractants so broadcast applications are needed.

It has been hypothesized that the effectiveness of the toxic food baits for rootworms could be greatly enhanced with the addition of volatile attractants (Metcalf et al., 1987). Several volatile chemical compounds have been identified that are differentially attractive to different species of rootworms. For example, the plant volatile constituent eugenol is attractive to the northern corn rootworm (Diabrotica barberi Smith & Lawrence) but not to the western corn rootworm (Diabrotica virgifera virgifera LeConte); whereas, estragole is attractive to the western corn rootworm but not to the northern species (Ladd et al., J. Econ. Entomol., 76:1049–1051, 1983; and Lampman et al., J. Chem. Ecol., 13:959–975, 1987). Various attractants for corn rootworms are presently being tested.

An attracticide formulation composed of the pheromone called Grandlure, feeding stimulants, and a toxicant has been developed for the boll weevil, Anthonomus grandis Boheman (Smith et al., J. Entomol. Sci., 25:838–843, 1990; and McKibben et al., pp. 303–304, In: Proceedings, Beltwide Cotton Production Research Conference, Jan. 9–14, 1990, Las Vegas, Nev., National Cotton Council of America, Memphis, Tenn., 1990). The formulation is used as a coating for a bait stick which is being field tested as a new, early and late season, control method for boll weevils.

There has been considerable research of the nocturnal behavior, including feeding behavior, of Helicoverpa/

Heliothis species and other noctuids. Results of nocturnal observations reported by Lingren et al., (Environ. Entomol., 23:562–570, 1977) indicated that peak feeding times for tobacco budworm adults occurred in early evening and early morning. Adler (Environ. Entomol., 16:424–427, 1987) reported intensive feeding by corn earworm adults on pigeonpea nectar at dusk in South Carolina. Observations of numerous, apparently newly-emerged corn earworm moths feeding in early evenings on the nectars of various wild flowers, especially *Gaura drummondii* (Spach), growing along the banks of the Rio Grande River during the spring as they moved from corn fields of origin in northern Mexico to breeding habitats in southern Texas were reported. See, for example, Beerwinkle, et al. (1994, Recent developments in attracticide research for Heliothis/Helicoverpa species, (pp. 224–237, In: Raulston, et al. [Eds.] Heliothis/Helicoverpa—1993 Supplement to the Five-Year National Research Action Plan for the Development of Suppression Technologies ARS-1994-6, Agricultural Research Service-USDA). Haynes et al. (J. Chem. Ecol., 17:637–645, 1990) and Heath et al. (Environ. Entomol., 21:845–859, 1992) identified volatile floral compounds attractive to cabbage loopers (*Trichoplusia ni* [Hübner]) in *Abelia grandiflora* Rehd and night-blooming jessamine (*Cestrum nocturum* L.), respectively. Landolt et al. (J. Econ. Entomol., 84:1344–1347, 1991) reported the attractance of cabbage loopers to the floral compound phenylacetaldehyde and described an attracticide system for this species which was composed of phenylacetaldehyde, sucrose, and methomyl combined in micropet dispensers. Several researchers (Tingle et al., J. Chem. Ecol., 16:2889–2898, 1990; Mitchell et al., J. Chem. Ecol., 17:259–266, 1991; and Tingle & Mitchell, J. Chem. Ecol., 18:907–914, 1992) have reported feeding and oviposition attractance of tobacco budworm adults to volatiles from cotton flowers and other host plants. Beerwinkle et al. (Environ. Entomol., 22:554–558, 1993) reported observations of intense early-evening feeding activity of corn earworm adults ≦1 d of age on ergot honeydew on infected dallisgrass growing adjacent to emergence habitats.

Based on extensive nocturnal observations of emergence and early post-emergence behavior which indicated that food seeking is a high priority activity of newly-emerged corn earworm adults, Lingren et al. (1987 and 1988) proposed the use of attracticides as an adult control technique. The viability of this technique was demonstrated by Lingren et al. (1990) who reported major mortalities among newly-emerged corn earworm adults that fed on attracticides which had been banded around corn stubble in an emergence habitat.

Laboratory bioassays have been conducted to determine the feeding attractiveness of several different plant species. Plants selected for testing have been those identified as naturally attractive food hosts by direct observation with the aid of night-vision equipment of adult corn earworm nocturnal feeding behavior or those identified indirectly by the analyses of residual pollen found on proboscides, antennae, and other body parts of moths (Lingren et al., J. Econ. Entomol., 86:1429–1439, 1993; and Environ. Entomol., 23:562–570, 1994). Additional plants have been selected for bioassay based on their observed attractiveness to other insect species.

Bioassays have been conducted primarily in olfactometers by means known in the art. See, for example, Beerwinkle, et al. (1994; and Southwest. Entomol., 21:305–405, 1996).

When plant volatile sources of different concentrations were tested against blanks in a two-choice olfactometer unit, the results were typically qualitative, indicating whether or not the plant volatiles were attractive, but failing to indicate a well defined dose/response relationship. In a series of assay tests of *Gaura suffulta* Engelm. bouquets of various sizes (bouquet sizes from 1 to 48 stems with one to three blooms per stem), all assays demonstrated moth attractance to the plants, but there were only slight differences in the comparative moth responses to the plant samples and the respective blanks for the different plant-sample sizes. However, when two different plant volatile attractants of varying concentrations were compared in the two-choice chambers, dose/response relationships were demonstrated. Similarly, the moth responses to variable concentrations of volatiles provided by different sized bouquets of the same plant in the six-choice olfactometer units tended to be proportional to the volatile concentrations, indicating clearly defined dose/response relationships (Beerwinkle et al. 1996). Six-choice units have been useful for assaying the relative attractiveness of up to six volatile sources in single tests. Typically, only 30 to 50 percent of the exposed moths responded to the volatile baits in overnight tests with this system.

The feeding attractiveness of volatiles from several different plant sources to corn earworm adults has been demonstrated (Beerwinkle et al. 1994). The flowering spikes of three different Gaura spp. and the honeydew exudates of ergot (*Claviceps paspali* [F. L. Stevens & J. G. Hall]) on dallisgrass (*Paspalum dilatatum* [Poir.]) seed heads have been observed to be attractive feeding hosts in the field, and the attractiveness of the volatiles from these sources has been confirmed in the laboratory. The three Gaura spp. of the family Onagraceae are night blooming plants whose blooms produce fragrant odors and nectar sources that apparently stimulate feeding by corn earworms and other noctuids. In contrast, the dallisgrass ergot honeydew has a musky odor that, to humans, is dissimilar to that from the blooms of the Gaura spp.

Pollen from willow (Salix spp.) and oak (Quercus spp.) were found on corn earworm moths indicating they had fed on those plants (Lingren et al. 1993, 1994). Flowering parts of coyote willow (*Salix exigua* Nutt.), black willow (*Salix nigra* Marsh.), post oak (*Quercus stellata* Wang.), and live oak (*Quercus virginiana* Miller) have been tested, and all were found to be attractive to corn earworm adults.

SUMMARY OF THE INVENTION

We have now developed compositions which are effective as attractants for a variety of economically important noctuids and other lepidopteran pests. This composition includes a mixture of effective amounts of the volatile compounds phenylacetaldehyde, methyl-2-methoxybenzoate, methyl salicylate, and optionally 2-phenylethanol and/or limonene. The present invention also provides methods for a reduction in noctuid and/or other lepidopteran species numbers or for their elimination, which includes attracting the insect species with the attractant composition. In the preferred embodiment, the attractant composition is used to pull the adult noctuid and/or other lepidopteran insects from the surrounding areas which may then be exposed to a lethal food source containing an insecticide, preferably with a feeding stimulant, on which the responding adults will feed.

In accordance with this discovery, it is an object of the present invention to provide a composition effective as an attractant to noctuid and/or other lepidopteran species.

Another object of the invention is to provide traps and controlled-release formulations containing the attractant composition.

A further object of the invention is to provide a method of reducing or preventing plant damage due to noctuid and/or other lepidopteran species using the attractant composition in combination with a feeding stimulant and insecticide.

Other objects, advantages and features of the invention will be readily apparent to one skilled in the art from the following description.

DETAILED DESCRIPTION OF THE INVENTION

The attractant compositions of the present invention are effective in attracting and controlling a variety of agronomically important adult insects of the order Lepidoptera. While pests of particular importance which are attracted to the compositions include noctuids such as *Trichoplusia ni* (cabbage looper), *Pseudoplusia includens* (soybean looper), *Heliothis virescens* (tobacco budworm), and *Helicoverpa zea* (corn earworm), and other lepidoptera such as *Diaphania hyalinata* (melonworm), and *Diaphania nitidalis* (pickleworm) other insects are effectively attracted to the attractants as well. For instance, chrysopids and coccinellids, which are natural predators of many noctuids and other lepidopteran pests, and scarabs are also attracted to the compositions. Without being limited thereto, it is envisioned that the attractants of this invention may be used to attract and control Lepidoptera including:

*Trichoplusia ni* (cabbage looper),
*Pseudoplusia includens* (soybean looper),
*Agrotis ipsilon* (black cutworm),
*Caenurgina erechtea* (forage looper),
*Helicoverpa zea* (corn earworm),
*Heliothis virescens* (tobacco budworm),
*Spodoptera frugiperda* (fall armyworm),
*Spodoptera exigua* (beet armyworm),
*Spodoptera ornithogalli* (yellowstriped armyworm),
*Anagrapha falcifera* (celery looper), and
*Pseudaletia unipuncta* (armyworm),
*Plutella xylostella* (diamondback moth),
*Achyra rantalis* (garden webworm),
*Desmia funeralis* (grape leaffolder),
*Diaphania hyalinta* (melonworm), and
*Diaphania nitidalis* (pickleworm), and
*Manduca quinquemaculata* (tomato hornworm),
*Manduca sexta* (tobacco hornworm),
*Eumorpha achemon* (achemon sphinx),
*Agrius cingulata* (sweetpotato hornworm), and
*Hyles lineata* (whitelined sphinx).

Furthermore, the attractant compositions of this invention are effective for attracting both sexes of adult Lepidoptera. Since female moths are the reproductive sex capable of laying eggs, the capture of females could serve as a major tool in reducing succeeding populations.

Compositions effective for use as attractants herein include a mixture of the plant volatile components phenylacetaldehyde, methyl-2-methoxybenzoate, methyl salicylate, and optionally 2-phenylethanol or limonene or both. Although compositions of only phenylacetaldehyde, methyl-2-methoxybenzoate, and methyl salicylate are attractive, efficacy is significantly improved by inclusion of at least one and preferably both of 2-phenylethanol and limonene. Suitable formulations may be prepared from these volatiles in isolated or impure form. However, as a practical matter, it is expected that substantially pure volatiles will be formulated with an inert carrier for use as an insect attractant composition. The practitioner skilled in the art will also recognize that these volatiles may be formulated in a single or separate compositions, and in liquid or solid form. Liquid carriers for use herein include but are not limited to water or organic solvents, such as polyols, esters, methylene chloride, alcohol (such as $C_1$–$C_4$ alcohol) or vegetable oil, although vegetable oils and alcohols are preferred. Suitable vegetable oils include olive oil, sesame oil, peanut oil, canola oil, cottonseed oil, corn oil, soybean oil, mineral oil, as well as methylated forms of these oils, or mixtures thereof. Aromatic and linear hydrocarbon solvents may also be included. The active ingredient mixture may also be incorporated in a solid substrate, such as clays, diatomaceous earth, silica, polyvinyl chloride, polystyrene, polyurethanes, ureaformaldehyde condensates, and starches. Other useful solid support matrices include expanded vermiculite and paraffinic or bees wax.

The amounts and concentrations of the volatile components, that is phenylacetaldehyde, methyl-2-methoxybenzoate, methyl salicylate, 2-phenylethanol, and limonene, are selected to provide an effective attraction of the insects. The effective amount is defined herein as that quantity of attractant that attracts the target insects to the location of a bait at a rate significantly higher than the attraction to a nonbaited location (i.e. negative control). Effective concentrations of the volatiles may vary between about 20–45% by weight phenylacetaldehyde, 0–30% by weight 2-phenylethanol, 0–30% by weight limonene, 15–40% by weight methyl-2 -methoxybenzoate, and 5–25% by weight methyl salicylate. Typically however, for improved attractancy the concentrations of the volatiles expressed as percent by weight will be as follows: phenylacetaldehyde in an amount of about 20–30%, preferably about 20–25%, more preferably about 22–24%, and most preferably about 23%; 2-phenylethanol in an amount of about 20–30%, preferably about 20–25%, more preferably about 21–23%, and most preferably about 22%; limonene in an amount of about 20–30%, preferably about 22–26%, more preferably about 23–25%, and most preferably about 24%; methyl-2-methoxybenzoate in an amount of about 15–25%, preferably about 18–22%, more preferably about 19–21%, and most preferably about 20%; and methyl salicylate in an amount of about 5–15%, preferably about 8–12%, more preferably about 9–11%, and most preferably about 10%. In one particularly preferred embodiment, the active ingredient mixture of the present invention contains approximately 23.51% by weight phenylacetaldehyde, 22.49% by weight 2-phenyl ethanol, 24.00% by weight limonene, 19.88% by weight methyl-2-methoxybenzoate, and 10.12% by weight methyl salicylate. In a further preferred embodiment, the active ingredient mixture of the present invention contains 5.77 mg/ml phenylacetaldehyde, 5.8 mg/ml limonene, 5.51 mg/ml 2-phenylethanol, 2.49 mg/ml methylsalicylate and 4.88 mg/ml methyl-2-methoxybenzoate. Limonene includes d- and l- forms as well as racemic mixtures.

The attractant composition may be further formulated with a variety of optional components or adjuvants, including but not limited to other plant volatiles, feeding stimulants, feed such as molasses, other insect attractants such as insect pheromones, or insect toxicants.

Yet other components which may be included in the formulation include humectants, preservatives, thickeners, antimicrobial agents, antioxidants, emulsifiers, film forming polymers and mixtures thereof. Additives which retard or slow the volatilization of the active mixture are preferred. Humectants may include polyols, sugars (such as molasses), glycols and hygroscopic salts. Antioxidants which protect the vegetable oils and reduce polymerization of phenyl acetaldehyde are preferred. Film forming polymers include gum rosin, latex, polyvinyl pyrrolidone, polyvinyl alcohol, polyvinyl chloride, polyethylene, polyvinyl acetate and mixtures thereof. Additional optional additives include, shellac, methyl methacrylate, and mixtures thereof.

In the preferred embodiment, feeding stimulants for the adult insects or moths are included in the attractant composition and function to induce the target insects to contact and/or ingest the bait, particularly when formulated with an insecticide to effect control. Without being limited thereto, feeding stimulants such as fructose, fucose, glucose, and particularly sucrose, are preferred.

Two basic responses promote adult feeding: proboscis extension and gustation. Proboscis extension is the critical initial response in feeding because a moth cannot feed unless its feeding tube (proboscis) is extended to contact the food source. Once the food source is contacted, other stimuli are involved in inducing the gustatory response which results in the ingestion of the food source. A measurable proboscis extension response has been demonstrated to different types of sugars and to the specific concentration of the sugar in solution. A distinct preference for sucrose has been demonstrated and its use is therefore preferred. Another source of sugar, feed grade molasses, that has been used previously as a feeding stimulant for corn earworm moths was not preferred. Furthermore and more importantly, for the development of adult control, it was found that there was a sustained proboscis extension response to highly concentrated sucrose (greater than or equal to about 2.5 M) solutions as well as an extended gustatory period due to the higher viscosity of the concentrated sucrose solution. Experiments conducted by applying the concentrated sucrose solution on the leaves of various crop plants such as field corn, sweet corn, green peppers, beans, and cabbage under field conditions indicated that the concentrated sucrose solution attained an equilibrium liquid phase which reflected the ambient relative humidity (RH); it became more concentrated in the afternoon when the RH was low, but absorbed water and became less concentrated in the evening as RH increased, while maintaining a liquid phase which induced adult moth feeding over a number of days after application. This phenomenon may be considerably improved and the sugar concentration decreased by use of thickeners, films, humectants, antimicrobial agents and other additives shown to be compatible with a sustained adult feeding response under field conditions.

Another important component of the adult control system of the present invention is inclusion of insect toxicants or pesticides that are highly toxic to the adult insects or moths, but do not significantly inhibit the attractance or feeding response when combined with a food source and applied to or in the vicinity (such as on plants or in a trap or bait station) of the crop plants treated with the feeding attractant.

Insect toxicants which may be included in the attractant composition include but are not limited to insecticides such as carbaryl, methomyl, acephate, thiodicarb, cyfluthrin, malathion, chlorpyrifos, emamectin benzoate, abamectin, spinosad, endosulfan, and mixtures thereof. Bacterial and viral pathogens may also be included, as well as insect growth regulators or compounds eliciting behavior modification or disrupting physiological functions. These may include, for instance, pigments and/or dyes which may mark, attract, modify various insect behaviors, or which may be toxic. Combination of the insecticide with the attractant composition of this invention and concentrated sucrose allows the use of significantly lower concentrations of insecticides to kill the adults under field conditions than would be used to control the insect pests with a normal commercial broadcast application of the same insecticides. Accordingly, one advantage of the present invention is a decrease in amount and concentration of insecticides required as compared with conventional insecticidal crop protection.

A variety of lepidopteran pheromones are suitable for use with the attractant composition. Overviews of the pheromones for many insects, including many Lepidoptera, which may be used herein have been described, and include, for example, Mayer and McLaughlin (Handbook of Insect Pheromones and Sex Attractants, CRC Press, Boca Raton, Fla., 1991) and Tamaki [Sex Pheromones, *In Comprehensive Insect Physiology Biochemistry and Pharmacology*, Vol. 9 Behavior, Kerkut and Gilbert (Ed.), Pergamon Press, New York, pp. 145–179].

Volatile or non-volatile extracts of Gaura or other plant species may also be included in the attractant composition. Suitable volatiles include but are not limited to one or more, but less than all, of the compounds selected from (E)-2-hexenal, (Z)-3-hexenol, (E)-2-hexenol, nonane, (Z)-3-hexenyl acetate, γ-terpinene, terpinen-4-ol, nerol, geraniol, eugenol, isoeugenol, γ-muurolene, valencene, 3,4-dihydro-8-hydroxy-3-methyl-1H-2-benzopyran-1-one, dodecyl acetate, methyl epijasmonate, 2-methylbutanal oxime, 2-methylbutanal (isomer A), 2-methylbutanal (isomer-B), cinnamaldehyde, benzyl alcohol, (E)-2-octenal, octanol, lilac aldehyde, an isomer of lilac aldehyde, lilac alcohol, an isomer of lilac alcohol, 2-phenyl-2-butenal, carvacrol, β-farnesene, α-selinene, selina-13,7(11)-diene, and benzyl benzoate, or mixtures thereof The attractant compositions may be used in a number of ways, including monitoring or controlling insect populations. In one preferred embodiment, the compositions may be placed within traps to monitor population changes. Precise monitoring will enable growers to reduce the number of insecticide applications when populations are low. In other preferred embodiments, the attractants may be used to control pest populations by employing large numbers of traps (trap-out strategy), or by combination with an effective amount of an insect toxicant or pesticide as described abovr to kill adult noctuids or other lepidopteran insects (as an attracticidal bait). Use in this manner should prove useful in suppressing target species before they can inflict damage to agronomically important crops.

In another embodiment, the attractant composition may be included as a part of traps or other solid supports which may also contain, be a part of or be in close proximity to a feeding stimulant, and/or an insecticide, pesticide, or other mechanical (such as a "bug zapper"), toxic or biologically active agent to eliminate, reduce, or prevent reproduction of the target insect species.

It is envisioned that the attractants may be used in conjunction with any type of appropriate trap or attractant disseminator as known in the art. The attractant can be applied or disseminated using a variety of conventional techniques, such as in an exposed solution, impregnated into a wicking material or other substrate, or incorporated in a deodorant dispenser. Further, the components of the attractant may be combined in a single dispenser provided within a single trap, or provided separately in a plurality of dispensers, all within a single trap. The attractant can be applied to the device undiluted, or formulated in an inert carrier. Volatilization can be controlled or retarded by inclusion of components as described above. Controlled, slow release over an extended period of time may also be effected by placement within vials covered with a permeable septum or cap, by encapsulation using conventional techniques, or absorption into a porous substrate.

One of ordinary skill will appreciate that the rate of release of the active ingredient mixture of the present invention may be varied by manipulation of the size of the reservoir and permeability of the matrix. The support or other delivery mechanisms of the present invention preferably provides release or volatilization of the active ingredient mixture of the invention for at least one week.

Application scenarios and methods of using the attractant composition of the present invention also include separate application of a feeding stimulant-insecticide mixture to plants by known methods with the placement of the attractant composition in a manner which will attract the noctuid and/or other lepidopteran species to the feeding stimulant-insecticide mixture. Placement may include location in a strip in the same field which is upwind of the strip of the feeding stimulant-insecticide mixture. The attractant composition of the present invention may be applied in or on granules, plastic dispensers or wicks, for example, and may be applied parallel to sprays of a feeding stimulant-insecticide mixture. Cross-wind application may offer greater control of the insect population because of an increase in the area with effective volatile concentrations, and the foraging and ovipositing behavior in which the moths fly upwind within the plant canopy. Single point application of the attractant composition may also be used effectively, depending on the existing wind conditions. Plants which may be protected from insect pests include but are not limited to agronomically important crops such as cotton and vegetables, including field corn, seed corn, sweet corn, cole crops, melons, and tomatoes.

In the practice of any of the above-described embodiments, an attractant is used as a trap bait or is otherwise applied to the locus of or in the vicinity of infestation in an amount effective to attract the target insect. Factors such as population density, precipitation, temperature, wind velocity, and release rate will influence the actual number of insects trapped.

The following examples are intended only to further illustrate the invention and are not intended to limit the scope of the invention, which is defined by the claims.

EXAMPLES

Feral male corn earworm moths, field-collected in pheromone-baited cone traps, have been used in the bioassay experiments when they were available. Laboratory-reared males and females from a colony maintained at the Crops Insects Research Unit at Weslaco, Texas, have also been used. While feral male moths have usually exhibited greater and more uniform response in the bioassays than have either the male or female laboratory-reared moths, overall responses of the feral and laboratory-reared moths have been similar. For example, in bioassay tests of goldenrod, *Solidago canadensis* L., the response of the feral males and the laboratory-reared males and females to the goldenrod baits were all significantly higher (ANOVA, $\alpha=0.01$) than their corresponding response to volatile blanks. While there was an apparent trend for increased positive responses to goldenrod volatiles among the groups (feral males>laboratory males>laboratory females), there were no statistically significant differences (ANOVA, $\alpha=0.05$) among the positive response levels for the three groups of moths to the goldenrod volatiles. Some variability in the response levels of both the feral and laboratory-reared moths, apparently related to season and short-term weather variations within seasons, has been observed. Bioassay results indicate that the active ingredient mixture of the present invention was highly attractive to moths during the spring and fall seasons, but comparatively unattractive during the summer. In one embodiment, therefore, the present invention provides a method of noctuid and/or other lepidopteran species control or plant protection from same which includes use of the active ingredient mixture of the present invention in at least one of spring or fall seasons.

The time-of-response during the night of testing, as detected with a night-vision equipped video system, varied somewhat with different volatile sources and different seasons of the year. However, response timing for feral and laboratory-reared males was similar. Response times for laboratory-reared females have been similar to that of the males.

Visual appearance has been suggested as a likely factor-contributing to the attractancy of potential food-host plants. Bioassay tests were conducted in two-choice chambers to determine the effects of sight on the attractancy of volatiles from *G. longiflora* bouquets. Similar bouquets of flowering *G. longiflora* were placed in each of the sample subchambers of the two-choice units. One of the bouquets was visible to the moths, and the other was prepared so it was invisible. The results indicated that visibility of the volatile sources was a significant factor (ANOVA, $\alpha=0.05$), but that the moth response due solely to olfactory stimuli was substantial. The attractant composition of the present invention may be present in a part of a trap or other form which is visually attractive to noctuid and/or other lepidopteran species, or may contain a component, such as a dye or pigment, which makes the composition more visually attractive to noctuid and/or other lepidopteran species.

To demonstrate the effectiveness of the present invention, chemical baits containing the active ingredient mixture of the present invention were tested in standard wire cone traps placed in alfalfa fields or in a pasture land adjacent to maturing or harvested cotton as further detailed below.

Predominant insect species captured during 48 trap nights/bait were soybean looper (*Pseudaplusia includens* Walker) (n=10392), cabbage looper (*Trichoplusia ni* Hubner) (n=8727), tobacco budworm (*Heliothis virescens* F.) (n=242), and corn earworm (*Helicoverpa zea* Boddie) (n=141). Melonworm (*Diaphania hyalinata* Linnaeus), a pyralidae, was captured in relatively large numbers (n=752). These chemical mixtures captured both sexes of these insects with approximately one-third to one-half of the total capture being females. The active ingredient mixture of the present invention, containing five chemicals, captured more moths of each species than phenylacetaldehyde alone or a mixture of the remaining four chemicals without phenylacetaldehyde.

Tests described herein were conducted to determine the attractiveness of some of these chemicals to corn earworm moths, other noctuid, and lepidopteran species in pheromone traps.

The active ingredient mixture of the present invention was tested in olfactometer tests individually and in various combinations. The five component mixture of phenylacetaldehyde, methyl salicylate, limonene, 2-phenylethanol, and methyl-2-methoxybenzoate were tested in relative amounts of 5.7%, 2.2%, 5.9%, 5.5% and 4.8% (weight volume), respectively.

In a test to determine the attractiveness of the attractant to corn earworm moths and other noctuids, standard wire pheromone traps (Hartstack et al., 1979) were placed in alfalfa fields or in pasture land adjacent to maturing or harvested cotton during September and October and September of the following year. Baits were prepared by dissolving chemicals in methylene chloride containing 50% canola oil so that the desired quantity of chemical or mixture of chemicals was obtained by dispensing one ml of the solution onto a cotton dental roll contained in a glass sleeve. While methylene chloride was used in these trials, the active ingredient mixture of the present invention may be delivered in other organic solvents, such as alcohols or oils, such as vegetable oils. Alternatively, the active ingredient mixture may be incorporated into a solid matrix, such as a clay, wax or polymer, so long as the active ingredient mixture remains volatile.

Baits prepared were the attractant mixture (100 mg per bait), phenylacetaldehyde (23 mg per bait), and the attractant containing no phenylacetaldehyde (77 mg per bait). One trap in each replicate was left unbaited. Phenylacetaldehyde was included as one treatment since it is contained in the active ingredient mixture of the present invention and has been implicated as an attractant for corn earworm and certain other noctuids (Cantelo and Jacobson, 1978, J. Environ. Sci. Health, A14:695–707; Haynes et al., 1991, J. Chem. Ecol., 17:637–646; Heath et al., 1992, Environ. Entomol., 21:854–859; and Pawar et al., 1983, ICN 8:27–28).

Positions of baits within each replicate were randomized on the first night, and were rotated one position each night to insure that each bait occupied each trap site during each test. Baits were placed in traps shortly before sundown by attaching the glass sleeve containing the treated cotton dental roll to the vertical rod holding the trap with a rubber band and pushing the cotton plug half way through the sleeve. Captured insects were removed from traps early the next morning, and captured insects were stored in a freezer until they were examined to determine species and sex. In a separate test, baits were prepared with individual chemicals to contain phenylacetaldehyde (23 mg per bait), methyl salicylate (10 mg per bait), limonene (24 mg per bait), methyl-2-methoxybenzoate (20 mg per bait) or 2-phenylethanol (22 mg per bait) and these baits were compared to the active ingredient mixture and unbaited traps. Counts were transformed using log (x+1) and analyzed using one way analysis of variance; means were separated using LSD with alpha=0.05.

Figure 1:
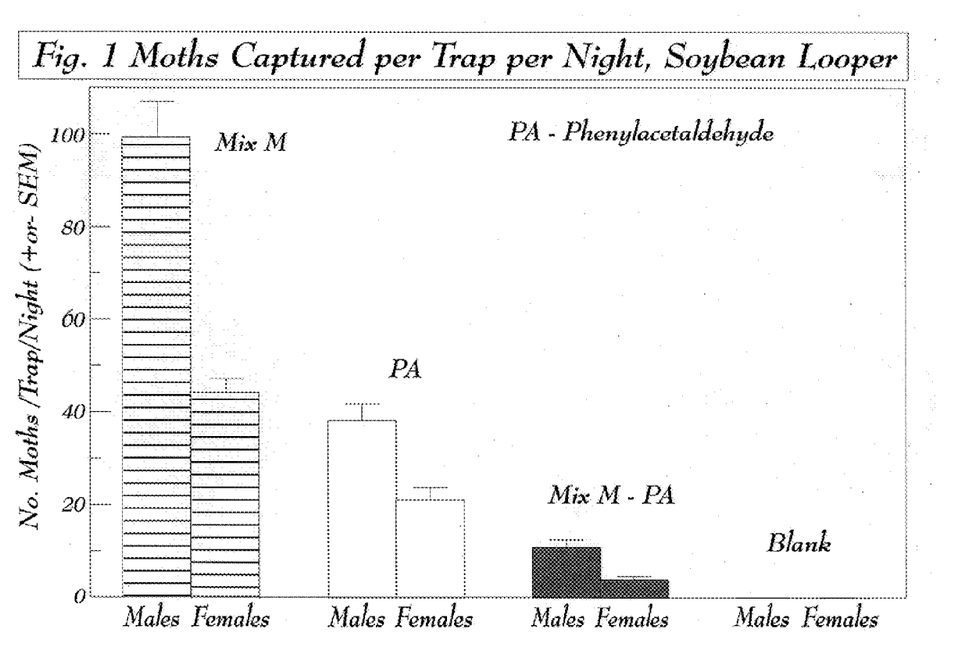
FIG. 1 shows results of the number of soybean looper moths captured per trap per night.

The predominant noctuid insect species captured during these tests were soybean loopers (*Pseudaplusia includens* Walker), cabbage loopers (*Trichoplusia ni* Hübner), tobacco budworm (*Heliothis virescens* F.), and corn earworms (*Helicoverpa zea* Boddie). Melonworm (*Diaphania hyalinata* Linnaeus), a pyralid/crambid was also captured in relatively large quantities. For soybean loopers, traps baited with the active ingredient mixture of the present invention captured an average of 143 moths per trap night (FIG. 1), which was significantly greater than captures with other baits. Traps baited with phenylacetaldehyde alone captured 59 moths per trap night, which was significantly more than the 15 soybean looper adults captured in traps baited with the active ingredient mixture of the invention without phenylacetaldehyde. Unbaited traps captured only two soybean looper moths (one male and one female) during the test period. More males (68%) than female (32%) soybean loopers were captured in traps baited with the chemicals. In total, 10,392 soybean loopers were captured during 48 trapping nights.

Figure 2:
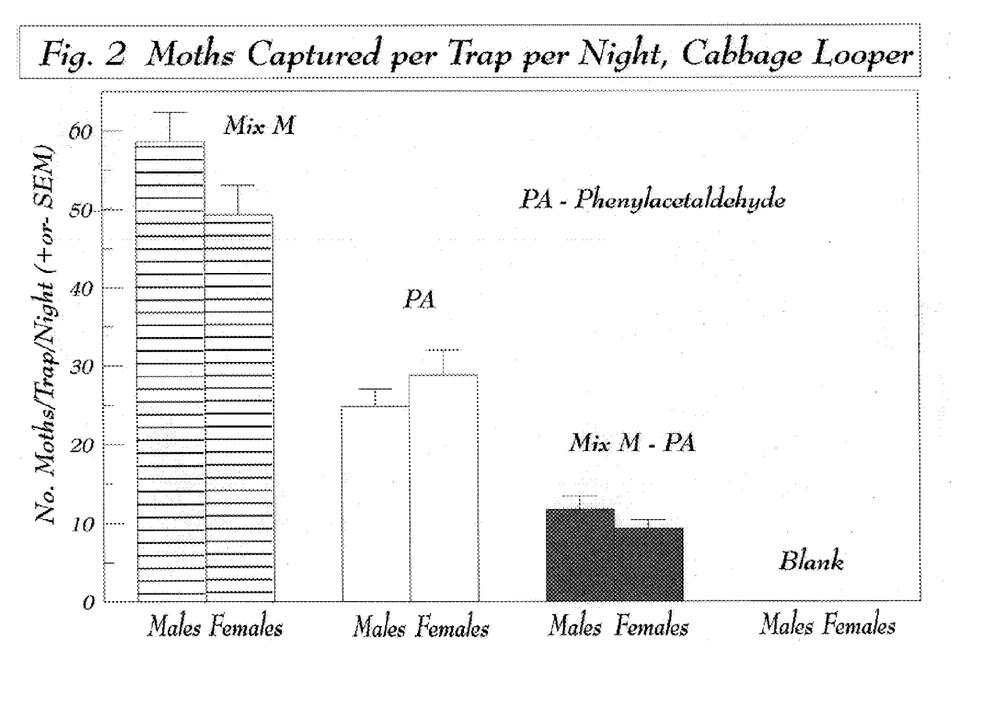
FIG. 2 shows results of the number of cabbage looper moths captured per trap per night.

Results were very similar for cabbage loopers in that trap captures were significantly different for all four treatments and in the same sequence (FIG. 2), with traps baited with the active ingredient mixture of the present invention capturing 108 moths per trap night, those baited with phenylacetaldehyde capturing 54 cabbage loopers trap night, and those baited with the active ingredient mixture containing no phenylacetaldehyde capturing 20 moths per trap night. Unbaited traps captured only 2 moths during the test. There was no significant difference in numbers of male and female cabbage looper moths captured in chemical-baited traps. Overall, 48% (n=8, 727) of the total cabbage loopers captured were females. Additionally, two traps baited with the active ingredient mixture were placed in a commercial cabbage field in Texas in September for one night, yielding 792 and 687 cabbage looper moths, 85% of which were females.

Figure 3:
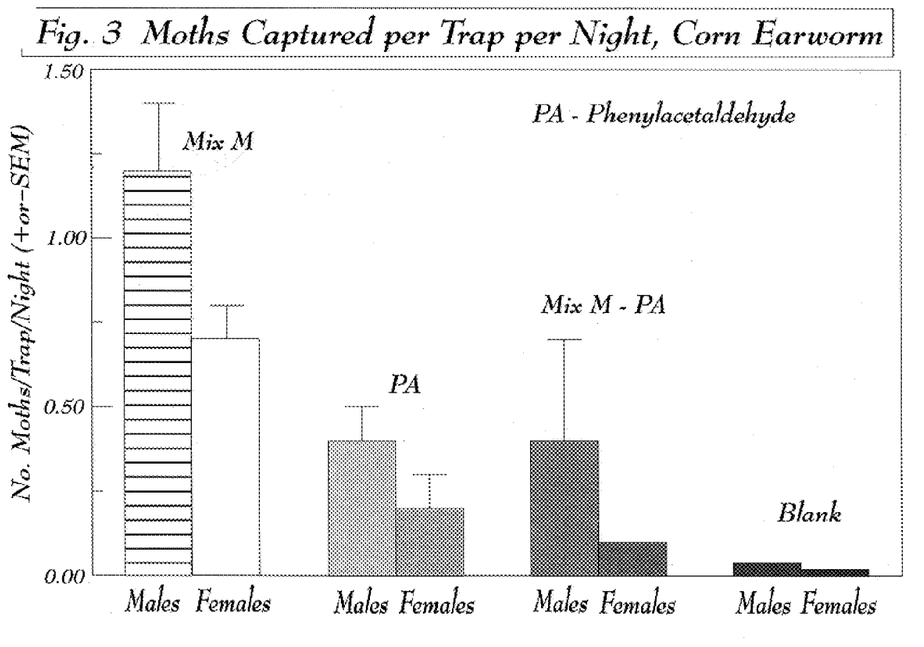
FIG. 3 shows results of the number of corn earworm moths captured per trap per night.

Traps baited with the active ingredient mixture captured more corn earworm moths than other treatments, although trap captures were low in all treatments (FIG. 3). Traps baited with the active ingredient mixture averaged 1.9 moths per trap night, with approximately 40% females. Less than 0.01 moths per night were captured in unbaited traps. Traps baited with phenylacetaldehyde or the active ingredient mixture without phenylacetaldehyde captured similar numbers of corn earworm moths. The numbers of corn earworms captured were similar to those captured in earlier tests when the traps were baited with bouquets of the Gaura flowers.

Figure 4:
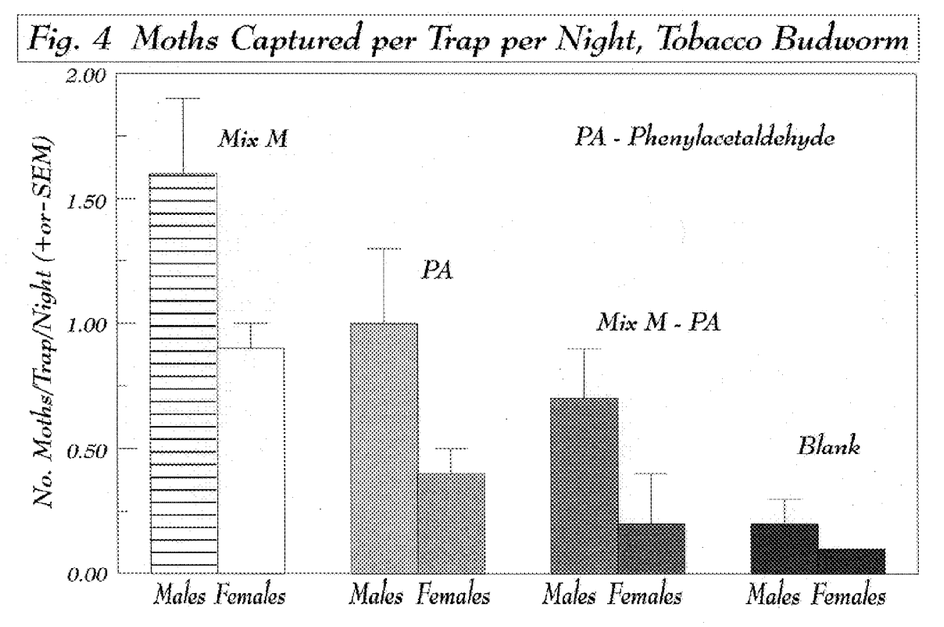
FIG. 4 shows the results of the number of tobacco budworms captured per trap per night.

Captures of tobacco budworm moths were also low, but more moths were captured in traps baited with the active ingredient mixture than with other baits or unbaited traps (FIG. 4). Traps baited with the active ingredient mixture averaged 2.5 moths per trap night, compared to 1.3 with phenylacetaldehyde, 1.0 with the active ingredient mixture without phenylacetaldehyde, and 0.3 in unbaited traps. Approximately 36% of tobacco budworm moths captured with the active ingredient mixture were females, which is significantly less than captures of males.

Figure 5:
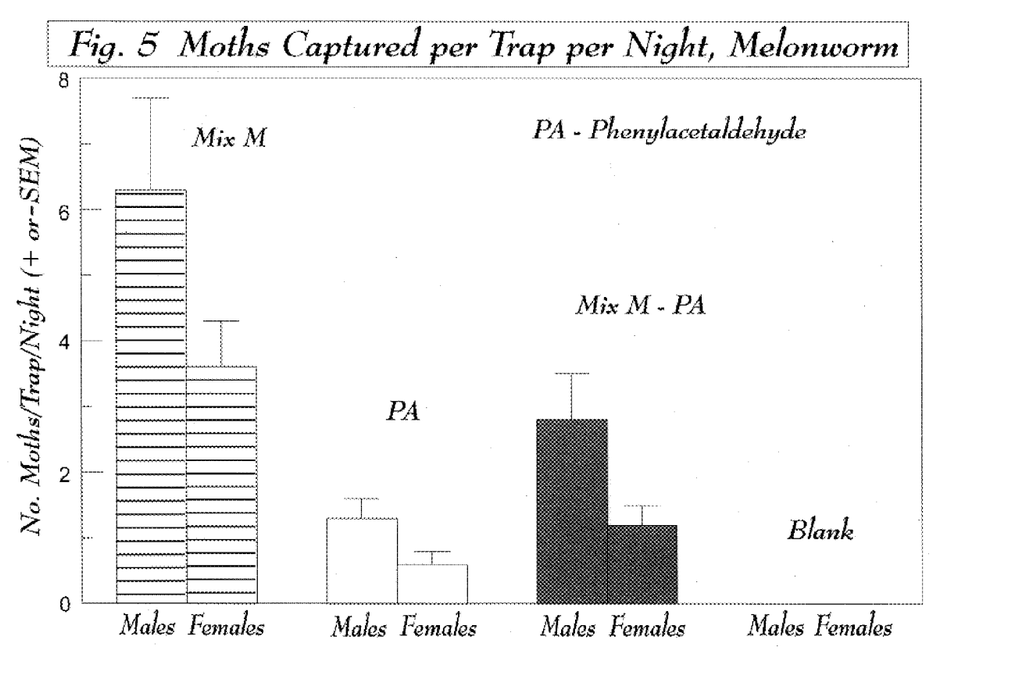
FIG. 5 shows the number of melonworm moths captured per trap per night.
Figure 6:
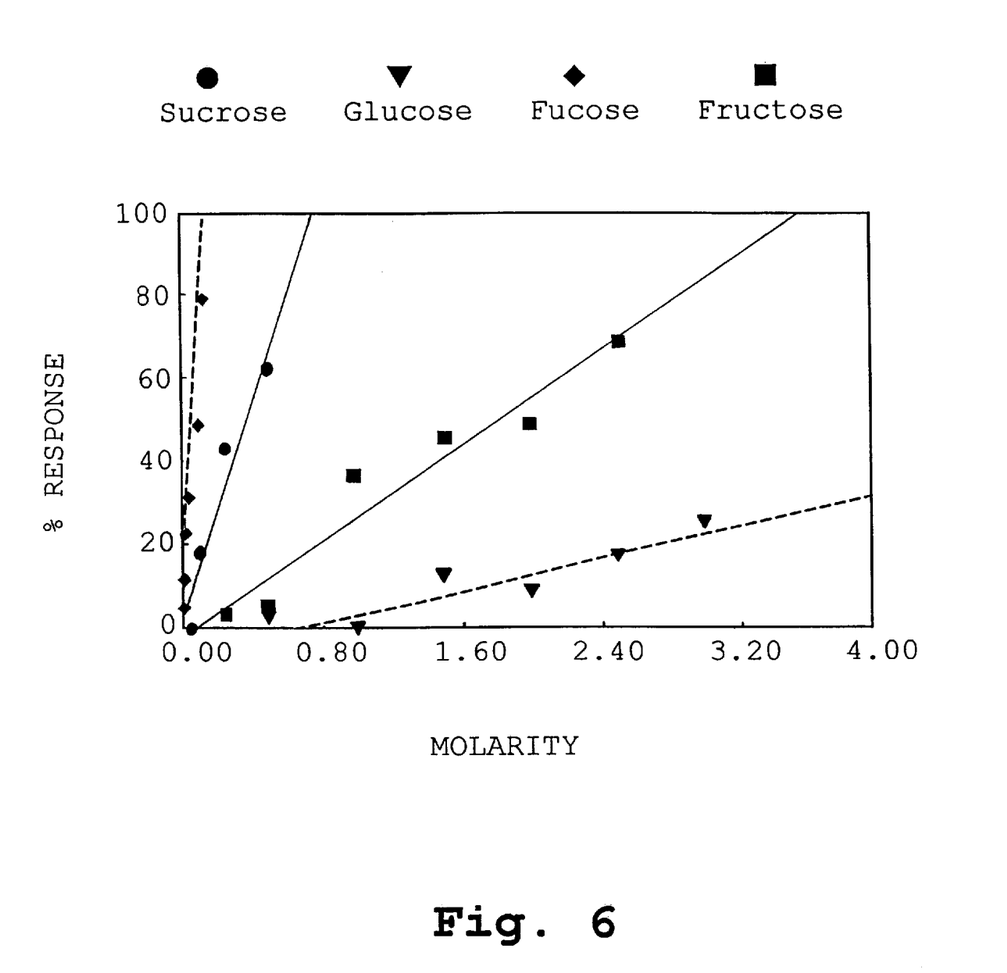
FIG. 6 shows the mean percentage proboscis extension response of *H. zea* males to different molar concentrations of sucrose, glucose, fucose and fructose.

Melonworm moths (a pyralid/crambid) were also captured in traps baited with the chemicals. Trap captures were significantly different for the four treatments, with the active ingredient mixture capturing the most, followed by the active ingredient mixture containing no phenylacetaldehyde, and then phenylacetaldehyde alone (FIG. 5). Unbaited traps captured no melonworm moths throughout the test period. There was no difference in captures of male and female melonworm moths in traps baited with the active ingredient mixture or the other chemical baits.

In tests comparing the active ingredient mixture with the individual chemicals contained in the active ingredient mixture (phenylacetaldehyde, methyl salicylate, 2-phenylethanol, methyl-2-methoxybenzoate, and limonene), none of the individual chemicals captured more than 1.0 tobacco budworm, corn earworm, or melonworm moths per trap night, which was no different than unbaited traps, except that phenylacetaldehyde captures of melonworm moths (4.4 moths per trap night) were greater than unbaited traps (o captured during test period). During this same period, the active ingredient mixture captured an average of 21.2 melonworm moths, 2.2 corn earworm moths and 3.0 tobacco budworm moths per trap night. The active ingredient mixture baited traps captured more cabbage looper (83.8 per trap night) and soybean looper (138.7 per trap night) moths than any of the individual chemicals. Phenylacetaldehyde baited traps caught more cabbage looper (56.9 per trap night) and soybean looper moths (79.4 per trap night) moths than any of the individual chemicals. Phenyl acetaldehyde baited traps caught more cabbage loopers (56.9) per trap per night than traps baited with methyl salicylate (5.3 and 2.3 per trap night, respectively), methyl-2-methoxybenzoate (1.5 and 3.0 per trap night, respectively) and 2-phenyl ethanol (3.7 and 0.5 moths per trap per night, respectively). Captures of cabbage looper moths and soybean looper moths with limonene (0.2 and 0.1 moths per trap night) were no different than captures of these species in unbaited traps (0 and 0.1 moths per trap night).

Even though traps baited with phenylacetaldehyde alone captured both sexes of cabbage looper and soybean looper moths, the addition of the other four chemicals in the active ingredient mixture significantly enhanced the attractiveness to these insects. Since this chemical mixture is attractive to both sexes of cabbage loopers in approximately equal amounts and captures about one-third as many female soybean looper moths as males, it has the potential for use in monitoring both sexes of these insects. Also, it has potential for use in adult control programs for these insect species by combining with a feeding stimulant and toxicant.

Because, major components of an attracticide using a feeding-based approach are the feeding attractant, feeding stimulant, toxicant or biologically-active materials, and a practical formulation, a major effort also involved in the development of this adult control technology was the evaluation of feeding stimulants. The purpose of the feeding stimulant is to induce feeding of the adults responding to the feeding attractant. The feeding stimulant should induce the insects to ingest or contact the stimulant so that a toxicant or biologically-active material contained in the stimulant will effect control.

Research conducted in the laboratory to identify an effective feeding stimulant involved two major responses: proboscis extension and gustation. Moths which feed through a tube-like apparatus called a proboscis that is normally coiled in the front of the head under resting condition have to uncoil the proboscis to feed. Proboscis extension is a response induced by contact of some parts of the insect having contact or tactile receptors, some of which are specific for the detection of feeding stimuli. Detection of suitable feeding stimuli causes the proboscis to be extended and to contact the food material. After the proboscis is extended and contact is made with the food material, other stimuli that are detected by external or internal receptors, induce the ingestion or gustatory response whereby the insect may secrete saliva through the proboscis and then suck the food material into the digestive system. Any toxicant or biologically-active material would then exert the control effect internally either to kill the insect or otherwise affect its physiology so that reproduction would be prevented. During the gustatory response, the insect, in most cases, maintains contact with the stimulant and the active ingredient so that detrimental effects on the adults may be enhanced by contact or by contamination of the insect's body.

Field evaluations of feeding stimulants involved both the proboscis extension and gustation responses because field feeding response was quantified on the basis of the number of moths feeding on different feeding stimulant treatments applied during early evening on parts of susceptible crops.

Adult bollworm or corn earworm, *Helicoverpa zea* (Boddie), were used in the laboratory evaluations of feeding stimulants. Both laboratory-reared and field-collected adults were used. Laboratory-reared adults were obtained from a culture begun from field-collected (blacklight-trapped or netted in attractive feeding areas) moths in the fall. No field-collected material was added to the culture during the evaluation period. Larvae were reared using ARTHRO FEED insect diet (Stonefly Industries, Bryan, Tex.). Field-collected adults were primarily males that were captured in sex pheromone (HERCON-ZEALURE, Hercon Environmental, Inc., Emigsville, Pa.) traps operated in cropping areas of the Brazos River Valley close to College Station, Tex. Captured males in trap canisters were brought into a shaded area (insectary or open shed) and given deionized water ad libitum on sanitary napkins prior to testing. Some field-collected females and males were obtained by digging pupae from senescent corn fields in the same cropping area and placing them in emergence containers in the ground inside natural saran screen cages which were checked daily for adult emergence and collection.

Although numerous different artificial and natural food materials were evaluated for feeding stimulant activity (feed-grade molasses, artificial sweeteners, sorghum molasses, plant nectar, honey, salts, etc.), the best materials identified included the sugars, sucrose, fructose, glucose, and fucose. Therefore, intensive evaluations were conducted with these. All evaluations were conducted on the basis of the molar concentration of each sugar in deionized water.

Testing for positive proboscis extension response was conducted by holding the wings of each adult together with the index finger and the thumb. The front tarsi (front legs) were touched to the test solutions in a porcelain multi-well plate by raking the front legs across it while minimizing contact of other body parts with the solution. While testing, the proboscis was observed for complete extension to contact the test solution. Partial extension was not considered a positive response.

Prior to testing, each insect was given deionized water *ad libitum* and then tested for a positive response to water alone. If a moth responded positively to water alone, it was discarded from further testing or was given water to satiation (no further response to water alone) before further testing. This procedure prevented consideration of an unspecific response to any kind of liquid as a positive proboscis extension response. Each moth was tested only once and discarded except for the laboratory-reared and the field-collected males and females emerging from pupae collected from senescent corn which were available in limited numbers as compared to sex pheromone-trapped males. These were tested only once a day, but were tested for more than one day.

A replicate consisted of the response of 10 individual insects to each treatment when each treatment was evaluated with consecutive insects rather than 10 insects being evaluated consecutively with the same treatment. A complete proboscis extension test consisted of 8 to 10 replicates.

Gustatory response was measured by weight rather than volume. Individual moths were placed on an apparatus in which an alligator clip was used to hold the moth's wings together so that the body axis was vertical. A hinged arm holding a 0.5 ml disposable plastic centrifuge tube was used to provide each insect with the test solution. The tube containing a test solution was held close to the insect's legs with the tube in the same plane as the insect. If contact of the front legs with the test solution did not induce extension of the proboscis and initiation of feeding, the proboscis was teased with an insect pin so that it contacted the test solution. If the solution was suitable for ingestion, the adults generally started feeding and fed for varying periods of time. When a moth stopped feeding and coiled its proboscis, the proboscis was teased again to contact the test solution at least once without resumption of feeding before the moth was considered to have fed to satiation. The amount ingested by each moth was determined by weighing the tube containing each test solution before and after feeding. To correct for weight loss due to evaporation, a check tube holding each test solution on which the moths did not feed, was weighed at the same time as the before and after feeding weights were determined. The amount ingested which was the difference in the before and after weights was corrected by subtracting the calculated percent loss due to evaporation.

Gustatory response to each test solution consisted of the mean weight ingested by 10 or more moths.

Evaluations were conducted in field plots of silking sweet corn (variety Kandy Korn) planted at about 10-day intervals in the spring at Texas A&M University Farm, Burleson County, Tex. Sections of a row 18 feet long were measured and marked off with flagging tape on the same row when sufficient moths were present for testing. Treatments were applied on consecutive sections of the row in a Latin Square design (Steele and Torrie, Principles and Procedures of Statistics, McGraw Hill, 1960) by randomly assigning treatments in the first replicate and rotating treatments so that treatment was at each location in each replicate.

Feeding stimulant test solutions were applied with a texture applicator gun used to apply wall texture. The spray system was pressurized with nitrogen gas in a metal cylinder. Operating the applicator gun under low pressure and regulating the flow of test material from the gun into the air stream with the size of the opening and the degree of retraction of the nozzle from the opening, it was possible to apply viscous test materials in relatively large droplets and with good coverage on the corn plants.

Test solutions were applied before sunset. Counts of the number of moths feeding in each row section were started at about sundown and were periodically made until the number observed started decreasing. To evaluate the longevity of the field treatment, counts of feeding moths were made at least up to the second night after application.

Results indicated that the highest response of the adults relative to concentration of the sugars evaluated was to fucose>sucrose>fructose>glucose (FIG. 6). Laboratory-reared females and males had a similar response to field-collected males and females except during the middle part of the growing season. At this time, field-collected adults had to be evaluated in the evening starting at dark and under red light to have a response similar to that of the laboratory-reared moths. Response of the laboratory-reared moths was not affected by evaluation conditions.

Because of the concentration of any feeding stimulant applied in the field would be expected to change in response to changes in environmental conditions (temperature, relative humidity, plant surface, etc.), the response to molar concentrations approaching the limits of solubility (saturation) of the different sugars was also evaluated. Although, these was an observed decrease in the percent proboscis extension response at the higher concentrations, response was still at a relatively high level at the highest concentrations evaluated (Table 1).

From an ingestion standpoint, a positive proboscis extension is the key criterion for a feeding stimulant because a moth cannot feed unless the proboscis is extended so any sugar not inducing proboscis extension in a high proportion of the moths tested was not evaluated further.

Because of the high percentage of proboscis extension response to fucose, the gustatory response might be expected to be elevated to this sugar. Unfortunately, and surprisingly, gustatory response to fucose was not significantly different than to water alone and did not show a dosage response (Table 2).

Gustatory response to comparable molar concentrations of sucrose and fructose was similar indicating that once the proboscis is extended, there is not much difference in gustatory response.

At the higher concentrations of sucrose, fructose, and glucose, approaching the solubility limits, gustatory response was similar to all three sugars even though the solutions were heavier and more viscous. These results verify that the controlling response relative to ingestion or gustation is the proboscis extension response, because when the proboscis extension response is bypassed by forcing contact of the proboscis with the sugars, there is no effect on the gustatory response.

Fructose and sucrose were evaluated for feeding response under field conditions because adults showed a consistently high response for both proboscis extension and gustation. Adult feeding response to sucrose was significantly higher than to a comparable concentration of fructose (Table 3).

The difference between the two sugars carried over into the second night, showing that sucrose remained suitable for inducing a feeding response at least for two nights after application.

The results of these evaluations show that sucrose is a suitable feeding stimulant for adult corn earworm. The sustained proboscis extension and gustatory responses at the higher concentrations, which are more practical for field application, have now been experimentally established. The residual suitability of field-applied sucrose for inducing feeding had not been previously reported.

All documents cited herein are incorporated herein by reference.

It is understood that the foregoing detailed description is given merely by way of illustration and that modifications and variations may be made therein without departing from the spirit and scope of the invention.

TABLE 1

Proboscis extension response of sex pheromone trap captured *Helicoverpa zea* males to high concentrations of sucrose and fructose

| Sugar | Concentration (Molarity) | Mean (±SD) % Response[3] |
|---|---|---|
| Sucrose (Test 1) | 0.5 | 35.0 ± 12.0c |
| | 1.0 | 67.5 ± 7.1a |
| | 1.5 | 55.0 ± 14.1ab |
| | 2.0 | 51.3 ± 11.3ab |
| | 2.5 | 48.8 ± 17.3bc |

TABLE 1-continued Proboscis extension response of sex pheromone trap captured
*Helicoverpa zea* males to high concentrations of sucrose and fructose

| Sugar | Concentration (Molarity) | Mean (±SD) % Response[3] |
|---|---|---|
| Sucrose (Test 2) | 1.0 | 50.7 ± 20.2b |
|  | 1.5 | 73.9 ± 11.6a |
|  | 2.0 | 56.4 ± 12.1b |
|  | 2.5 | 52.0 ± 12.1b |
| Fructose | 0.5 | 25.5 ± 12.0c |
|  | 1.0 | 41.8 ± 13.2bc |
|  | 2.0 | 59.0 ± 17.3ab |
|  | 3.0 | 60.9 ± 13.8a |
|  | 4.0 | 59.1 ± 13.0ab |
|  | 5.0 | 51.8 ± 19.4ab |

[3]Means in the same column in different tests for sucrose and fructose followed by different letters are significantly different according to Turkey's Standardized Range (HSD) Test ($\alpha = 0.05$).

TABLE 2

Mean number of milligrams ingested of different concentrations
of fucose by sex pheromone trap-captured *Helicoverpa zea* males

| Concentration (Molarity) | Mean ± SD No. mg Ingested per Adult (N) |
|---|---|
| 0.25 | 17.7 ± 10.5(30) |
| 0.50 | 21.3 ± 18.0(30) |
| 1.00 | 16.4 ± 13.6(29) |
| 1.50 | 15.5 ± 12.2(30) |
| 2.00 | 13.7 ± 6.6(30) |
| 2.50 | 12.9 ± 6.4(29) |

TABLE 3

Mean number of adult *Helicoverpa zea* feeding per plot treated with
sucrose (2.5M), fructose (5.0M), or untreated

| Night | Time | X ± SE per plot* | | |
|---|---|---|---|---|
|  |  | Sucrose | Fructose | Untreated |
| First | 2120 | 12.0 ± 2.4a | 7.2 ± 1.6b | 0.3 ± 0.2c |
|  | 2140 | 10.3 ± 3.2a | 3.0 ± 1.1b | 0.5 ± 0.2b |
|  | 2200 | 6.5 ± 1.8a | 2.3 ± 0.6b | 0.3 ± 0.2b |
|  | 2220 | 4.5 ± 1.6a | 0.8 ± 0.4b | 0.0 ± b |
|  | 2240 | 1.5 ± 0.6a | 1.5 ± 0.2a | 0.0b |
|  | Overall | 7.0 ± 1.1a | 3.0 ± 0.6b | 0.2 ± 0.1c |
| Second | 2100 | 6.8 ± 1.7a | 3.7 ± 0.6a | 0.0b |
|  | 2125 | 6.2 ± 1.1a | 3.0 ± 0.5b | 0.0c |
|  | 2150 | 4.8 ± 0.8a | 1.8 ± 0.3b | 0.2 ± 0.2c |
|  | 2220 | 2.5 ± 0.7a | 1.5 ± 0.4a | 0.0 ± b |
|  | Overall | 5.1 ± 0.6a | 2.5 ± 0.3b | 0.0 ± 0.0c |

*Means for the same time or overall for each night followed by different letters are significantly different according to LSD ($\alpha = 0.05$).

We claim:

1. An attractant composition for adult noctuid or other lepidopteran species comprising a mixture of about 20–45% by weight phenylacetaldehyde, 0–30% by weight 2-phenylethanol, 0–30% by weight limonene, 15–40% by weight methyl-2-methoxybenzoate, and 5–25% by weight methyl salicylate.

2. The composition of claim 1 wherein the concentration of phenylacetaldehyde is between about 20–30% by weight, the concentration of 2-phenylethanol is between about 20–30% by weight, the concentration of limonene is between about 20–30% by weight, the concentration of methyl-2-methoxybenzoate is between about 15–25% by weight, and the concentration of methyl salicylate is between about 5–15% by weight.

3. The composition of claim 1 wherein the concentration of phenylacetaldehyde is between about 20–25% by weight, the concentration of 2-phenylethanol is between about 20–25% by weight, the concentration of limonene is between about 22–26% by weight, the concentration of methyl-2-methoxybenzoate is between about 18–22% by weight, and the concentration of methyl salicylate is between about 8–12% by weight.

4. The composition of claim 1 further comprising at least one compound selected from the group consisting of (E)-2-hexenal, (Z)-3-hexenol, (E)-2-hexenol, nonane, (Z)-3-hexenyl acetate, γ-terpinene, terpinen-4-ol, nerol, geraniol, eugenol, isoeugenol, γ-hydroxy-3-methyl-1H-2-benzopyran-1-one, dodecyl acetate, methyl epijasmonate, 2-methylbutanal oxime, 2-methylbutanal, cinnamaldehyde, benzyl alcohol, (E)-2-octenal, octanol, lilac aldehyde, an isomer of lilac aldehyde, lilac alcohol, an isomer of lilac alcohol, 2-phenyl-2-butenal, carvacrol, β-farnesene, α-selinene, valencene, and benzyl benzoate.

5. The composition of claim 1 further comprising at least one of a feeding stimulant, additional insect attractant, feed, or insect toxicant.

6. The composition of claim 5 wherein said additional attractant is an insect pheromone.

7. The composition of claim 1 further comprising an inert carrier.

8. The composition of claim 1 further comprising a humectant, antioxidant, preservative, emulsifier, film forming polymer or mixtures thereof.

9. The composition of claim 1 further comprising methylene chloride, N-methyl pyrrolidone, $C_1$–$C_4$ alcohol, a polyol, sugar, glycol, hygroscopic salt, vegetable oil, polyvinyl pyrrolidone, polyvinyl alcohol, polyvinyl chloride, polyethylene, polyvinyl acetate or mixtures thereof.

10. A controlled release formulation comprising the composition of claim 1 in a carrier selected from the group consisting of clay, expanded vermiculite, wax, cellulose acetate, starch, hydrophobic polysiloxane, and mixtures thereof.

11. A trap for adult noctuid or other lepidopteran species comprising the composition of claim 1.

12. A method of reducing plant damage due to noctuid or other lepidopteran species comprising providing an effective amount of the composition of claim 1 in the vicinity of the locus of said noctuid or other lepidopteran insects.

13. The method of claim 12 wherein said noctuid or other lepidopteran species are selected from the group consisting of cabbage loopers, soybean loopers, corn earworms, tobacco budworms, pickleworms and melonworms.

14. The method of claim 12 wherein said composition is provided in the vicinity of said plant.

15. The method of claim 12 wherein said composition is provided in combination with a feeding stimulant.

16. The method of claim 12 wherein said composition is provided in combination with an insect toxicant.

17. The method of claim 14 wherein said plant is selected from the group consisting of cotton, vegetables, field corn, seed corn, sweet corn, cole crops, melons, and tomatoes.

* * * * *